United States Patent [19]

Foll et al.

[11] Patent Number: 5,496,899
[45] Date of Patent: Mar. 5, 1996

[54] CROSSLINKABLE POLYMER MATERIAL WHICH MAY BE USED IN NON-LINEAR OPTICS AND PROCESS FOR OBTAINING IT

[75] Inventors: Franck Foll, Carnon Ouest; Dominique Bosc, Lannion; Julienne Liang, Fresnes; Alain Rousseau; Bernard Boutevin, both of Montpellier, all of France

[73] Assignee: France Telecom, Paris, France

[21] Appl. No.: 298,318

[22] Filed: Sep. 1, 1994

[30] Foreign Application Priority Data

Sep. 6, 1993 [FR] France .................. 93 10572

[51] Int. Cl.$^6$ .................................................. C08F 8/30
[52] U.S. Cl. ................... 525/327.2; 525/327.3; 525/327.4; 525/376; 526/270; 526/273; 526/298; 526/312
[58] Field of Search ............ 525/327.2, 327.3, 525/328.4; 526/270, 273, 298, 312

[56] References Cited

U.S. PATENT DOCUMENTS

| | | | |
|---|---|---|---|
| 5,231,140 | 7/1993 | Kilburg et al. | 525/376 |
| 5,266,651 | 11/1993 | Foss et al. | 525/327.3 |
| 5,290,824 | 3/1994 | Mandal et al. | 525/293 |
| 5,294,463 | 3/1994 | LeBarny et al. | 427/488 |
| 5,332,520 | 7/1994 | Bach et al. | 526/318 |
| 5,384,378 | 1/1995 | Etzbach et al. | 526/298 |
| 5,393,644 | 2/1995 | Etzbach et al. | 526/273 |

FOREIGN PATENT DOCUMENTS

| | | |
|---|---|---|
| 2630744 | 4/1988 | France . |
| 2246138 | 7/1990 | United Kingdom . |

OTHER PUBLICATIONS

Mandal et al, "Novel photo-crosslinked nonlinear optical polymers", Makromol. Chem., Rapid Commun. 12, 63–68 (1991).

Francis et al. "Isocyanate Cross–Linked Polymers for Non-linear Optics", Chem. Mater. 1993, 5, 506–510.

Muller et al, "Quadratic non–linear optical properties of thermally cross–linkable polymers", Synthetic Metals, 54, (1993), 139–146.

Primary Examiner—Bernard Lipman
Attorney, Agent, or Firm—Larson and Taylor

[57] ABSTRACT

The invention relates to a crosslinkable material that is active in non-linear optics, containing a polymer which carries chromophores each included in a polymer unit of formula:

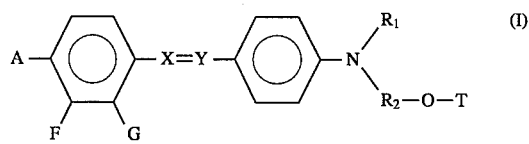

in which:

T is part of the polymer chain,
A is an —$NO_2$, —CN or —C(CN)=C(CN)$_2$ group,
$R_1$ is a hydrogen atom or a methyl or ethyl group,
$R_2$ is a $CH_2$, $C_2H_4$, $C_3H_6$ or $C_4H_8$ group, and:
  either X=Y is an azo group, F being a hydrogen atom and G being a group —C(O)— O—W or a group —C(O)—O—(CH$_2$)$_n$—O—W, n being an integer between 2 and 6 and W being a hydrogen atom or a dimerizable group,
  or X=Y is an azomethine group, one of the groups F and G being a group —O—W or —R$_3$—O—W, $R_3$ being a group —O—C(O)—R$_4$— or —O—R$_4$—, where $R_4$ is a $C_1$ to $C_6$ alkyl, the other of the groups F and G being a hydrogen atom and W being a hydrogen atom or a dimerizable group.

18 Claims, 1 Drawing Sheet

CROSSLINKABLE POLYMER MATERIAL WHICH MAY BE USED IN NON-LINEAR OPTICS AND PROCESS FOR OBTAINING IT

The present invention relates to the active materials in non-linear optics, which are used in particular in the field of optical signal telecommunications and optical signal processing. For example, these materials may be used for generating harmonics, frequency translation, optical memories, optical modulators, optical amplifiers, and the like.

Among the various materials which may be used in non-linear optics, polymerized organic materials are of competitive performance relative to inorganic materials such as gallium arsenide and lithium niobate.

Indeed, the organic materials make it possible to manufacture multilayer integrated optical circuits by techniques already tried and tested on electronic integrated circuits (in particular photolithography), in contrast to the inorganic materials, which have to be used in the form of monocrystals. The consequence of this is a lower manufacturing cost for the optical components.

Furthermore, hybridization of the organic materials is easier than in the case of the inorganic materials.

In addition, the organic materials allow much faster signal processing than the inorganic materials, because of their much greater rate of change of state.

Finally, in the case where these materials are used in an optical modulator, the organic materials make it possible to reduce the control voltage and the length of interaction between the light wave and the control electric field, thereby allowing easier use and a greater flow of information.

The polymers which may be used in non-linear optics are generally used in film form. They are composed of a carbon skeleton onto which optically non-linear side groups (ONLG) or chromophoric groups are attached. In order for the material to be active in non-linear optics, the ONLGs must be oriented so as to render the medium non-centrosymmetric.

This orienting is done using a polarizing electric field perpendicular to the polymer film, at a voltage in general of the order of 100 V/$\mu$m of film thickness or greater, while the material is heated at a temperature in the region of, or slightly above, its glass transition temperature.

When the material is cooled to a temperature below its glass transition temperature, the ONLGs retain their orientation imposed by the electric field. However, little by little the ONLGs lose this orientation with time, and all the more rapidly the lower their glass transition temperature. Since the glass transition temperature is never very high, the polymer material thus has non-linear optical properties that are unstable with time.

In addition, a rise is generally seen in the temperature of the optical components during their use, which further accelerates the process of orientation relaxation of the ONLGs.

In order to overcome this instability, it has been attempted to block the ONLGs, after they have been oriented, by chemical bonds.

Thus, it was endeavoured to block ONLGs by involving them in the polymerization process, while maintaining an orienting electric field during the polymerization. However, it is particularly difficult to control simultaneously the polymerization and orientation of the ONLGs under the effect of the electric field, in the region of the glass transition temperature. In addition, the ONLG concentrations which may thus be obtained are relatively low.

Moreover, document FR-A-2,630,744 discloses a polymer material which may be used in non-linear optics, in which the ONLGs are maintained oriented by a crosslinking of the polymer which is performed during the application of an electric field for polarization of the ONLGs, after polymerization. However, the crosslinking is obtained by bonds between the carbon skeletons of the polymerized chains and not by chemical bonds which concern the ONLGs directly. Consequently, the mobility of the ONLGs, although hampered by the crosslinking, is nonetheless not suppressed.

B. K. Mandal et al. (Makromol. Chem. Rapid Commun., 12, 63–68 (1991)) have proposed to dope a polymer possessing photo-crosslinkable groups with a dye which is active in non-linear optics, which formed the ONLGs of the polymer and which possessed these same photo-crosslinkable groups at its two ends. The crosslinking thus made it possible to block the ONLGs themselves by crosslinking after polarization but, even in the words of the authors, this system had to be optimized in order to be made use of. In particular, the ONLG concentrations which could be obtained thereby were low.

S. Muller (thesis from the University of Paris VI, of 1st July 1992) has disclosed a polymer which may be used in non-linear optics, in which the ONLGs could be interlinked by heating during their polarization by an electric field. However, the electrooptic coefficients obtained were too low. Indeed, according to a plausible hypothesis, the reaction of anchoring of the ONLGs occurred before their effective orientation had taken place.

Cécil V. Francis et al. (Chem. Mater., 1993, 5, 506–510) have disclosed a material which may be used in non-linear optics, obtained by reaction between tolonate HDT (a triisocyanate) and a chromophore which possessed a hydroxyl group at one end and an amine function at its opposite end. The chromophores were mixed with the tolonate HDT and heated to 50° C., which brought about the reaction of the amine function with certain isocyanate groups of the tolonate HDT, giving oligomers capable of forming a film. The film was then heated to 75° C. during application of an electric field for polarization of the chromophores, which brought about the crosslinking of the film material by reaction between the hydroxyl groups of the chromophores and the remaining isocyanate groups of the tolonate HDT. However, the material obtained has a mediocre electrooptic coefficient.

The aim of the present invention is especially to stabilize the ONLGs after they have been oriented, in order to obtain a polymer which may be used in non-linear optics and which has both good non-linear optical properties and great stability at high temperature, with a sufficient ONLG concentration.

To this effect, the subject of the invention is a crosslinkable material that is active in non-linear optics and that contains a polymer having a chain on which are laterally grafted chromophores that are active in non-linear optics and that may be oriented under the effect of a polarizing electric field, the said chromophores containing an anchoring functional group for stabilizing the orientation of the chromophores by crosslinking, characterized in that each chromophore is included in a unit of the polymer which correspond to the following formula (I):

in which:

T is part of the polymer chain,

A is an $-NO_2$, $-CN$ or $-C(CN)=C(CN)_2$ group, $R_1$ is a hydrogen atom or a methyl or ethyl group, $R_2$ is a $CH_2$, $C_2H_4$, $C_3H_6$ or $C_4H_8$ group, and:

either X=Y is an azo group (X and Y are nitrogen atoms), F being a hydrogen atom and G being a group $-C(O)-O-W$ or a group $-C(O)-O-(CH_2)_n-O-W$, n being an integer between 2 and 6 and W being a hydrogen atom or a dimerizable group, G then constituting the abovementioned anchoring functional group, or X=Y is an azomethine group (X is a CH group and Y is a nitrogen atom, or X is a nitrogen atom and Y is a CH group), F being a group $-O-W$ or $-R_3-O-W$, W being a hydrogen atom or a dimerizable group, $R_3$ being a group $-O-C(O)-R_4-$ or $-O-R_4-$, where $R_4$ is a $C_1$ to $C_6$ alkyl, and G being a hydrogen atom, F then constituting the said anchoring functional group, or X=Y is an azomethine group (X is a CH group and Y is a nitrogen atom, or X is a nitrogen atom and Y is a CH group), G being a group $-O-W$ or $-R_3-O-W$, W being a hydrogen atom or a dimerizable group, $R_3$ being a group $-O-C(O)-R_4-$ or $-O-R_4-$, where $R_4$ is a $C_1$ to $C_6$ alkyl, and F being a hydrogen atom, G then constituting the said anchoring functional group, the said material additionally containing at least one complementary anchoring functional group capable of attaching itself to the anchoring functional group carried by the chromophore during the crosslinking.

The chromophores are oriented using a polarizing electric field, and they are then blocked in their oriented position by thermochemical or photochemical crosslinking, by bonding the anchoring functional group of the chromophores with the complementary crosslinkable functional group.

The crosslinked polymer material obtained has an excellent electrooptic coefficient and its optical characteristics display great stability at high temperature.

Another subject of the invention is this crosslinked polymer material.

According to an advantageous embodiment of the invention, when X=Y is an azomethine group and when F is a group $-R_3-O-W$, $R_3$ is a group $-O-R_4-$.

According to another advantageous embodiment of the invention, when X=Y is an azomethine group and when G is a group $-R_3-O-W$, $R_3$ is a group $-O-(O)-R_4-$.

The polymer unit which comprises the chromophore may be chosen from the acrylate or methacrylate family or from the styrene family, from the α-haloacrylate family, from the ketone family or from the vinyl ether family.

In particular, the unit of the polymer which comprises the chromophore may have one of the following formulae:

and $Z_1$ being a hydrogen, fluorine or chlorine atom or a methyl group and ONLG representing the chromophore.

The polymer may contain, besides the unit which comprises the chromophore, at least one additional unit, the unit which comprises the chromophore representing a molar proportion of between 10 and 50% of the units of the polymer.

These additional units may be chosen from the acrylate or methacrylate family, from the styrene family, from the vinyl ester family, from the vinyl ether family or from the vinyl carbonate family.

These additional units may comprise the complementary anchoring functional group.

Furthermore, these additional units serve to adjust the thermomechanical properties of the material and to adjust the concentration of the chromophores, in order to determine the optical properties of the material.

The complementary anchoring functional group may also be carried by additional molecules, intimately mixed with the polymer which carries the chromophore. These additional molecules may be either polymerized molecules, one unit of which includes the complementary anchoring functional group, or molecules each carrying two complementary anchoring functional groups which are preferably identical, the radical which carries the two complementary anchoring functional groups preferably being a $C_1$ to $C_{10}$ alkyl or aryl radical.

According to a first embodiment of the invention, G is a $-COOH$ group and constitutes the anchoring functional group of the chromophore and the complementary anchoring functional group is an isocyanate, epoxide, hydroxyl or $-SH$ group.

The crosslinking reaction is then triggered by heating, during application of the polarizing electric field.

In this embodiment, the polymer may advantageously contain, besides the unit which comprises the chromophore, at least one unit which has the following formula (III):

where:

$Z_3$ is a hydrogen, fluorine or chlorine atom or a methyl group, and m is an integer between 1 and 6.

According to a second embodiment of the invention, one of the groups F and G contains an alcohol function and constitutes the anchoring functional group of the chromophore, the complementary anchoring functional group being an isocyanate, —COOH or acid chloride group.

The crosslinking reaction is then triggered by heating, during application of the polarizing electric field.

In this embodiment, the polymer may contain, besides the unit which includes the chromophore, at least one unit which has the following formula (IV):

(IV)

According to a third embodiment of the invention, W is a dimerizable group chosen from the group comprising:

$Z_2$ being a hydrogen, fluorine or chlorine atom or a methyl group, and the complementary anchoring functional group also containing a dimerizable functional group chosen from the same group as W.

The dimerizable groups of the anchoring functional group carried by the chromophore and of the complementary anchoring functional group are preferably identical.

For these various groups W, the dimerization reaction is triggered by insolation, immediately after application of the polarizing electric field. However, in the case of the group —C(O)—C($Z_2$)=CH$_2$, the reaction may also be triggered by heating during application of the polarizing electric field.

In this embodiment, generally, the anchoring functional groups carried by the chromophores constitute at least some of the complementary anchoring functional groups, the crosslinking being effected at least partly by dimerization between chromophores. The crosslinking could possibly even be done exclusively by dimerization between chromophores.

In order to prepare the material that is active in non-linear optics, a preferred route consists in polymerizing a monomer of following formula (VI):

(VI)

in which A, F, G, $R_1$ and $R_2$ are as defined above and M is a group chosen from the family of acrylic, methacrylic and styrene radicals.

Another subject of the invention is this monomer.

In particular, M may have one of the following formulae:
—C(O)—C($Z_1$)=CH$_2$, $Z_1$ being a hydrogen, fluorine or chlorine atom or a methyl group, and:

When X=Y is an azo group, the monomer of formula (VI) may be obtained from the compounds (VIII)

and (IX)

by a process comprising first a step of diazotization of the compound (VIII) in order to obtain a diazonium salt of this compound, followed by a coupling step between the said diazonium salt and the compound (IX).

When M is a group from the family of the acrylic or methacrylic radicals (that is to say in particular when M corresponds to the formula —C(O)—C($Z_1$)=CH$_2$, $Z_1$ being as defined above), the compound (IX) may be prepared by esterification between the compound (X)

and the acid M—OH or its acid chloride.

When M is a styrene group, the compound (IX) may be prepared by reaction between the compound (X) and chloromethylstyrene, with phase transfer catalysis (PTC).

When G is a group —C(O)—O—(CH$_2$)$_n$—OH, the production of this group may comprise an esterification step of a compound Br—(CH$_2$)$_n$—OH with a carboxyl group.

This esterification may take place either on the monomer (which is preferable) or on the polymer or on the above-mentioned compound (VIII).

When G is a group C(O)—O—W and —O—W is a dimerizable carboxyl group, G may be obtained by reaction between a —COOH group located initially in place of the group G on the chromophore and an acid chloride Cl—W, which gives the anhydride G.

When G is a group C(O)—O—(CH$_2$)$_n$—O—W and —O—W is a dimerizable carboxyl group, the production of this group G may comprise an esterification step between the alcohol and the acid chloride Cl—W in order to obtain the compound (XI):

Br—(CH$_2$)$_n$—O—W, followed by an esterification step between the compound (XI) and a carboxyl group located initially in place of the group G in the chromophore.

The group G may be formed in this way either on the monomer (which is preferable) or on the polymer or on the abovementioned compound (VIII).

When X=Y is an azomethine group, the monomer may be obtained by one of the following three routes:

(a) reaction between (b) reaction between (c) reaction between

In routes (b) and (c), the diamine may be obtained from the alkylated para-nitroaniline by reduction of —NO$_2$ to —NH$_2$.

When X=Y is an azomethine group and —O—W is a dimerizable carboxyl group, the grafting of W may be carried out by reaction of the acid chloride Cl—W with a hydroxyl group of the chromophore.

Another subject of the invention is the use of one of the materials according to the invention in an optical component.

The materials according to the invention may be used in all the applications of non-linear optics, in particular modulators.

Furthermore, they may be used in linear optics in order to produce optical read-only memories, in particular when the crosslinking is photochemical. Indeed, after polarizing the chromophores, it is then possible to crosslink the polymer material locally using a beam of light, in particular laser, and then to remove the polarization in the non-crosslinked zones by heating all of the material. It is thus possible to engrave information on a flat support, for example an optical disc.

Two specific embodiments of the invention, given without any limitation being implied, will now be described, with regard to the attached drawing in which.

EXAMPLE 1

1°) Synthesis of 2-(N-ethylanilino) ethyl methacrylate

This synthesis is carried out from 2-(N-ethylanilino)ethanol according to the following reaction scheme:

8.7 g (equivalent to 0.0527 mol) of 2—(N-ethylanilino)ethanol, 5.33 g (equivalent to 0.0527 mol) of triethylamine, a few ppm of hydroquinone and 150 cm$^3$ of chloroform are mixed at room temperature in a 250 cm$^3$ two-necked flask fitted with a condenser and a dropping funnel.

6.05 g (equivalent to 0.0579 mol) of methacryloyl chloride (Cl—C(O)—C(CH$_3$)=CH$_2$) are added dropwise. Once the addition is complete, the solution is heated at 45° C. for 24 hours. The temperature of the mixture is allowed to return to room temperature, followed by washing twice with 150 cm$^3$ of water. The organic phase is dried over sodium sulphate and the solvent is stripped off. The alcohol-ester mixture is chromatographed on silica, the eluent used being dichloromethane. 2-(N-Ethylanilino)ethyl methacrylate is obtained, in the form of a yellow oil, with a yield of 65%.

The product obtained was analysed by $^1$H NMR, 200 MHz (solvent: CD$_3$COCD$_3$) $\delta$=1.2 ppm (3H, t); 1.95 (3H, s); 3.45 (2H, quart.); 3.7 (2H, t); 4.3 (2H, t); 5.6 (1H, d); 6.1 (1H, s); 6.6-6.8-7.2 ppm (5H, aromatic protons).

2°) Synthesis of 3-nitro-6-(4'-(N-(2-methacryloxyethyl)-N-ethylamino)benzoic acid This synthesis first comprises a step of diazotization of 3-nitroanthranilic acid (marketed by Maybridge Co, Limited, UK), according to the reaction scheme:

This step is followed by a coupling stage of the diazonium salt obtained with 2-(N-ethylanilino)ethyl methacrylate according to the reaction scheme:

85 cm³ of 0.3N sodium hydroxide solution (equivalent to 0.0257 mol) and 6 g (equivalent to 0.0257 mol) of 3-nitroanthranilic acid are mixed in a 250 cm³ single-necked flask. It is necessary to heat to 60° C. in order to dissolve the acid, if need be adding a small amount of water. 11 cm³ of 10N hydrochloric acid solution (equivalent to 0.11 mol) are then added dropwise with vigorous mechanical stirring. The solution is cooled slowly to a temperature between 0° C. and 5° C., followed by dropwise addition, with vigorous stirring, of 1.77 g (equivalent to 0.0257 mol) of sodium nitrite in 5 cm³ of water. The mixture is left stirring for 2 hours 30 minutes at 5° C. and then filtered on a Büchner funnel.

The filtrate is then added dropwise, at room temperature, to a solution of 2-(N-ethylanilino)ethyl methacrylate (obtained by esterification of 2-(N-ethylanilino)ethanol, sold by Aldrich) in 20 cm³ of ethanol. The colour immediately turns red. A precipitate forms after a few minutes. The mixture is left stirring overnight and the solution is then filtered on a Büchner funnel. The solid fraction is washed with water and then with pentane. Thin layer chromatography on silica indicates the formation of a single product (eluent, $CH_2Cl_2$/ether: 9/1, product formed: red spot at $R_f=0.49$).

In order to remove the remaining traces of nitroanthranilic acid, the product is purified by chromatography on silica, using a dichloromethane/ether (9/1) mixture as eluent. The yield is 49%. The melting point of the product is 115° C.

The product obtained was analysed by proton NMR at 200 MHz in $CDCl_3$: $\delta=1.3$ (3H, t); 1.9 ppm (3H, s); 3.6 ppm (2H, quart.); 3.8 ppm (2H, t); 4.4 ppm (2H, t); 5.6 ppm (1H, s); 6.1 ppm (1H, s); 6.9–9.1 ppm (7H, aromatic protons).

The AB system of the signals at 6.8 ppm and 7.7 ppm of the aromatic ring carrying the tertiary amine should be noted. This shows that the electrophilic substitution of the diazonium salt on this ring occurs in position 4 relative to the amine function.

3°) Preparation of the crosslinkable copolymer

This copolymer is obtained by radical polymerization in solution in THF (tetrahydrofuran) at 60° C. for 36 hours with AIBN (azobisisobutyronitrile) as initiator.

1.405 g (equivalent to $3.3\times10^{-3}$ mol) of 3-nitro-6-(4'-(N-(2-methacryloxyethyl)-N-ethylamino) benzeneazo)benzoic acid, 1.0925 g (equivalent to $7.7\times10^{-3}$ mol) of glycidyl methacrylate and 0.18 g (equivalent to $1.1\times10^{-3}$ mol) of AIBN are added to 25 ml of TBF in a tube fitted with a threaded joint.

After nitrogen-vacuum degassing for half an hour, the tube is closed and placed in a thermostatted bath. Stirring is provided by a magnetic bar. Once the polymerization time has elapsed, the reaction mixture is precipitated in 800 ml of methanol. The copolymer is taken up in dichloromethane, filtered and dried for 24 hours at 40° C. under 20 mm Hg. 1.92 g of copolymer are thus recovered, equivalent to a yield of 77%. The molar masses measured with PMMA standards are Mw=3400 and Mn=1250. The composition of the copolymer determined by $^1$H NMR and elemental analyses is as follows: the copolymer obtained contains 26% of units comprising ONLG and 74% of glycidyl methacrylate units (in molar percentages).

The glass transition temperature is approximately 70° C.

4°) Electrooptic characterization and stability

Copolymer films are prepared on a plate coating machine, with thicknesses of the order of 1.2 to 1.5 μm, on a suitable glass substrate (for example B K 7). They are subjected to a perpendicular electric field by the corona effect. The conditions for orienting the ONLGs are about 100° C. and 5 kV for the corona voltage (with a distance of 1 cm between the electrode and the film) for a few minutes. The electrooptic coefficient $d_{33}$, obtained by the Maker fringes, is of the order of 50 pm/V (picometers per volt), which is an excellent value.

Such a sample is not stable since the ONLGs have not been crosslinked at this temperature. Thus, as may be seen in FIG. 1 (dotted curve), if it is reheated without application of the electric field, the intensity of the second harmonic emitted by the non-linear optical effect collapses as soon as the film exceeds about 90° C.

Figure 1:
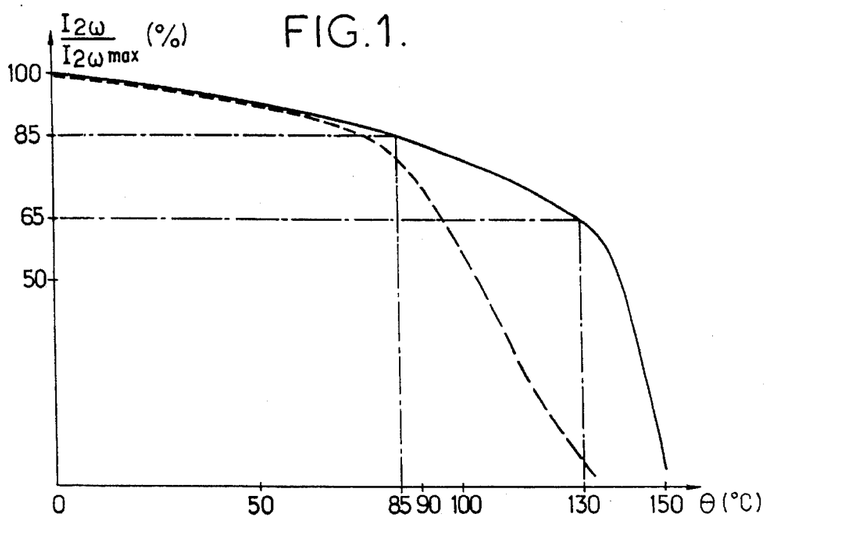
FIG. 1 represents the intensity of the second harmonic $I_{2\omega}$ of a material according to the invention, relative to its intensity immediately after polarization $I_{2\omega}$ max ($I_{2\omega}/I_{2\omega}$ max in %), as a function of temperature ($\theta$ in ° C.), with and without crosslinking (as the continuous line and the dotted line respectively), and FIGS. 2 and 3 each represent absorption spectra of a material according to the invention, before polarization, after polarization without crosslinking and after crosslinking respectively.

In contrast, if, following the orientation, it is subjected to an annealing at 130° C. for 3 hours while maintaining the electric field, the ONLGs are crosslinked while maintaining the orientation. This provides a much greater stability.

Thus, as represented in FIG. 1 (solid line curve), the generation of the second harmonic has decreased by only 15% in 1 hour at 85° C., and by 35% at 130° C.

However, the orientation is reduced by the cross-linking, which forces the dipoles to position themselves in directions which are not always those of the polarizing electric field. Thus, the electrooptic coefficient $d_{33}$ passes, after crosslinking at 130° C. for 1 hour, from 50 pm/V to 20 pm/V, which is still a satisfactory value.

Figure 2:
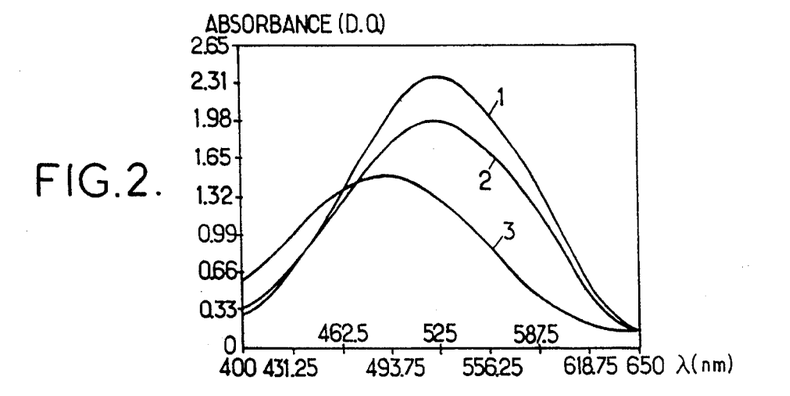
Figure 3:
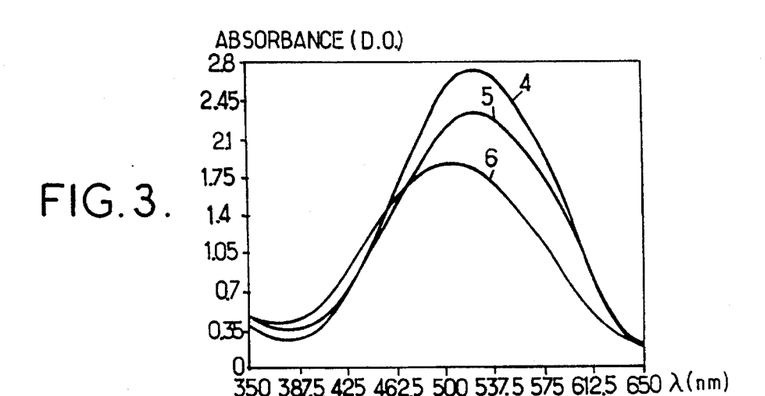

5°) Demonstration of the crosslinking between the carboxyl and epoxy groups by absorption spectrometry FIGS. 2 and 3 represent the absorption spectra (absorbance in optical density units as a function of the wavelength in nanometers) of a copolymer film obtained as indicated in 3° above.

The film is prepared on a plate coating machine, is then rendered uniform by annealing at a temperature close to its glass transition temperature, the chromophores are then oriented by a corona electric field, slightly above the glass transition temperature, and the orientation is fixed by crosslinking, while heating markedly above the glass transition temperature, under a corona electric field.

In FIGS. 2 and 3, the absorption spectrum of the film is measured at the end of the annealing step, at the end of the orientation step and at the end of the crosslinking step, under the following conditions:

FIG. 2:

Curve 1: after annealing at 75° C. for 15 min,

Curve 2: after orientation in a corona electric field of 8 kV at 1 cm from the film, at 90° C. for 30 min, Curve 3: after crosslinking in the corona electric field at 140° C. for 30 min and then at 160° C. for 30 min,

FIG. 3:

Curve 4: after annealing at 70° C. for 45 min,

Curve 5: after orientation in a corona electric field of 8 kV at 1 cm from the film, at 80° C. for 90 min, Curve 6: after crosslinking in the corona electric field at 130° C. for 30 min.

It is observed in FIGS. 2 and 3 that the absorbance of the film decreases after the orientation step, which confirms that the chromophores are well oriented. Furthermore, the absorbance peak of the film is shifted towards the low wavelengths, which confirms that the carboxyl groups have reacted with the epoxy groups.

EXAMPLE II

Grafting of a photodimerizable group onto 3-nitro-6-(4'-(N-(2-methacryloxyethyl)-N-ethylamino)-benzeneazo) benzoic acid

Furylacrylic acid (marketed by Aldrich) and excess thionyl chloride, $SOCl_2$, are first reacted together at reflux for several hours in order to obtain furylacrylic acid chloride.

The remaining thionyl chloride is distilled off at 20 Torr at room temperature, followed by distillation of the furylacrylic acid chloride at 49° C. and at 0.9 mbar.

Furylacrylic acid chloride is thus obtained with a yield of approximately 80% and a purity of approximately 99%.

The furylacrylic acid chloride, dissolved in carbon tetrachloride, is subsequently reacted with bromopropanol in pyridine, at 50° C. for 24 hours.

The bromopropyl ester of furylacrylic acid is thus obtained:

with a degree of conversion of 85%.

The bromopropyl ester of furylacrylic acid is subsequently reacted with 3-nitro-6-(4'-(N-(2-methacryloxyethyl)-N-ethylamino)benzeneazo)benzoic acid, in the presence of DBU (1,5-diazabicyclo[5.4.0]undec-7-ene, marketed by Aldrich) and DMF (dimethylformamide). The following compound is thus obtained, with a yield greater than 30%:

which compound may be polymerized with a comonomer carrying a group and then crosslinked by insolation immediately after orientation of the chromophores by a polarizing electric field.

What is claimed is:

1. A crosslinked material that is active in non-linear optics, obtained by crosslinking a crosslinkable material that contains a polymer having a chain on which are laterally grafted chromophores that are active in non-linear optics and that may be oriented under the effect of a polarizing electric field, the said chromophores containing an anchoring functional group for stabilizing the orientation of the chromophores by crosslinking after their polarization by an electric field, wherein each chromophore is included in a unit of the polymer which corresponds to the following formula (I):

in which:

T is part of the polymer chain,

A is an —$NO_2$, —CN or —C(CN)=C(CN)$_2$ group, $R_1$ is a hydrogen atom or a methyl or ethyl group, $R_2$ is a $CH_2$, $C_2H_4$, or $C_3H_6$ or $C_4H_8$ group, and:

either X=Y is an azo group, F being a hydrogen atom and G being a group —C(O)—O—W or a group —(O)—O—(CH$_2$)$_n$—O—W, n being an integer between 2 and 6 and W being a hydrogen atom or a dimerizable group, G then constituting the above-mentioned anchoring functional group or X=Y is an azomethine group, F being a group —O—W or —R$_3$—O—W where W is a hydrogen atom or a dimerizable group, R$_3$ being a group —O—C(O)—R$_4$— or —O—R$_4$— where R$_4$ is a $C_1$ to $C_6$ alkyl, and G being a hydrogen atom, F then constituting the said anchoring functional group Or X=Y is an azomethine group, G being a group —O—W or —$R_3$—O—W, where W is a hydrogen atom or a dimerizable group, $R_3$ being a group —O—C(O)—$R_4$— or —O—$R_4$—, where $R_4$ is a $C_1$ to $C_6$ alkyl, and F being a hydrogen atom, G then constituting the said anchoring functional group, the said polymer additionally containing at least one complementary anchoring functional group capable of attaching itself to the anchoring functional group carried by the chromophore during the crosslinking, said crosslinked material being obtained by crosslinking of said crosslinkable material after polarization of its chromophores by an electric field, the crosslinking being obtained by chemical bonding between the anchoring functional group carried by the chromophore and the complementary anchoring functional group.

2. The material as claimed in claim 1, wherein X=Y is an azomethine group and F is a group —$R_3$—O—W, $R_3$ being a group —O—$R_4$.

3. The material as claimed in claim 1, wherein X=Y is an azomethine group and G is a group —$R_3$—O—W, $R_3$ being a group —O—C(O)—$R_4$.

4. The material as claimed in claim 1, wherein the chromophore is included in a unit of the polymer which is chosen from acrylates, methacrylates and styrenes.

5. The material as claimed in claim 1, wherein the chromophore is included in a unit of the polymer which is chosen from haloacrylates, ketones and vinyl ethers.

6. The material is claimed in claim 1, wherein the polymer contains, besides the unit which comprises the chromophore, an additional, the unit which comprises the chromophore representing a molar proportion of between 10 and 50% of the units of the polymer.

7. The material as claimed in claim 6, wherein the additional unit is chosen from the acrylate or methacrylate family, from the styrene family, from the vinyl ester family, from the vinyl ether family or from the vinyl carbonate family.

8. The material as claimed in claim 6, wherein the complementary anchoring functional group is included in the additional unit.

9. The material as claimed in claim 1, wherein G is a —COOH group which constitutes the anchoring functional group of the chromophore and the complementary anchoring functional group is an isocyanate, epoxide, hydroxyl or -SH group.

10. The material as claimed in claim 9, wherein the chromophore is included in a unit of the polymer which has the following formula (II):

11. The material as claimed in claim 9, wherein the polymer contains besides the unit which includes the chromophore, at least one unit which has the following formula (III):

where:
 $Z_3$ is a hydrogen, fluorine or chlorine atom or a methyl group, and
 m is an integer between 1 and 6.

12. The material as claimed in claim 11, wherein $Z_3$ is a methyl group and m is equal to 1.

13. The material as claimed in claim 1, wherein one of the groups F and G contains an alcohol function and constitutes the anchoring functional group of the chromophore, the complementary anchoring functional group being an isocyanate, —COOH or acid chloride group.

14. The material as claimed in claim 13, wherein the polymer contains, besides the unit which includes the chromophore, at least one unit which has the following formula (IV):

15. The material as claimed in claim 1, wherein W is a dimerizable group chosen from the group comprising:

$Z_3$ being a hydrogen, fluorine or chlorine atom or a methyl group, and the complementary anchoring functional group also containing a dimerizable functional group chosen from the same group as W.

16. The material as claimed in claim 15, wherein the dimerizable groups of the anchoring functional group carried by the chromophore and of the complementary anchoring functional group are identical.

17. The material as claimed in claim 16, wherein the anchoring functional groups carried by the chromophores constitute at least some of the complementary anchoring functional groups, the crosslinking being effected at least partly by dimerization between chromophores.

18. The material as claimed in claim 17, wherein the unit including the chromophore has the following formula (V):

* * * * *

UNITED STATES PATENT AND TRADEMARK OFFICE
CERTIFICATE OF CORRECTION

PATENT NO. : 5,496,899
DATED : March 5, 1996
INVENTOR(S) : FOLL, et al

It is certified that error appears in the above-indentified patent and that said Letters Patent is hereby corrected as shown below:

Column 12, in formula (I), change "-X-Y-" to -- -X=Y- --.

Column 12, at the end of line 58, change "-(O)-" to -- -C(O)- --.

Column 13, line 41, after "additional" insert --unit--.

Column 14, in formula (III) change "n" to --m--.

Signed and Sealed this

Twenty-fifth Day of June, 1996

*Attest:*

BRUCE LEHMAN

*Attesting Officer*     *Commissioner of Patents and Trademarks*